United States Patent [19]

Medcalf

[11] 4,051,187

[45] Sept. 27, 1977

[54] METHOD OF PRODUCING AMINOPHENOL USING A RHODIUM/CARBON CATALYST WITH SYNERGISTIC QUANTITIES OF RHODIUM, TRICHLORIDE OR RHODIUM TRIBROMIDE

[75] Inventor: Eugene Medcalf, Sommerville, N.J.

[73] Assignee: Oxamine, Inc., Mount Vernon, N.Y.

[21] Appl. No.: 680,174

[22] Filed: Apr. 26, 1976

Related U.S. Application Data

[63] Continuation-in-part of Ser. No. 555,428, March 5, 1975, abandoned.

[51] Int. Cl.² .............................................. C07C 91/44
[52] U.S. Cl. .................................. 260/575; 260/580; 260/582; 252/441
[58] Field of Search ................... 260/575, 580, 582; 252/447, 441

[56] References Cited

U.S. PATENT DOCUMENTS 2,823,235  2/1958  Penrose et al. .................. 260/580
3,383,416  5/1968  Benner .................................. 260/575
3,678,108  7/1972  Arrigo et al. ..................... 260/580 X
3,694,508  9/1972  Baron et al. ........................ 260/575
3,754,014  8/1973  Kober et al. ..................... 252/441 X
3,876,703  4/1975  Harmetz et al. .................... 260/575

FOREIGN PATENT DOCUMENTS 1,009,024  11/1965  United Kingdom ................ 260/575
1,028,078  5/1966  United Kingdom ................ 260/580

*Primary Examiner*—Daniel E. Wyman
*Assistant Examiner*—John J. Doll
*Attorney, Agent, or Firm*—Karl F. Ross

[57] ABSTRACT

A semicontinuous or continuous process for producing para-aminophenols by the hydrogenation of corresponding nitrobenzenes wherein a catalyst containing about 5% platinum-group metal wherein about 10 to 80% of said platinum-group metal is in the form of $RhCl_3$ and from 20 to 90% of said platinum-group metal is in the form of elemental Rh, Pd, Pt, or Ru and where the balance of said catalyst comprises carbon to convert substantially all of the nitrobenzene to a para-aminophenol in an aqueous phase containing the latter.

4 Claims, No Drawings

METHOD OF PRODUCING AMINOPHENOL USING A RHODIUM/CARBON CATALYST WITH SYNERGISTIC QUANTITIES OF RHODIUM TRICHLORIDE OR RHODIUM TRIBROMIDE

CROSS-REFERENCE TO RELATED APPLICATION

This application is a continuation-in-part of Ser. No. 555,428 filed Mar. 5, 1975 (now abandoned).

FIELD OF THE INVENTION

The present invention relates to an improved method of making para-aminophenols in high yield and of high quality, e.g. suitable for acetylation to produce an acetylated para-aminophenol which has been found to be an effective chemical and pharmaceutical intermediate for use in dyes and in analgesics, photographic compositions and rubber processing and compounding.

Para-aminophenol has been produced by reducing nitrobenzene with hydrogen in the presence of aqueous sulfuric acid on a catalyst consisting of platinum or palladium or mixtures thereof at temperatures ranging from 60° C to 120° C as described inter alia in U.S. Pat. No. 3,383,416.

According to this patent, the reduction of the nitrobenzene is interrupted prior to completion and sufficient unreacted nitrobenzene is permitted to remain after termination of the reaction to form a nitrobenzene phase or layer containing the catalyst suspended therein while the other or aqueous phase, containing the para-aminophenol, is removed. The reaction system, consisting of the two phases, is generally removed from the reaction vessel entirely and subjected to separation elsewhere, care being taken to avoid exposure of the catalyst to air.

While processes of this type have been successful heretofore in that they do indeed efficiently produce para-aminophenol, they have not been fully satisfactory because of erratic performance and utilize catalysts which do not have sufficient yield or selectivity.

OBJECTS OF THE INVENTION

It is an object of this invention to provide an improved hydrogenation catalyst for use in the manufacture of para-aminophenol.

It is a further object to significantly increase the rate of hydrogenation to nitrosobenzene and/or phenylhydroxylamine without concurrently causing the hydrogenation to proceed to aniline.

SUMMARY OF THE INVENTION

It is known that different "activators" can modify catalyst behavior in terms of conversion of starting material as well as selectivity to the desired product. Some activators will cause hydrogenation to take place rapidly, resulting in a rapid conversion of starting material and a rapid formation of a desired product. A catalyst of this type is considered to be a selective catalyst. However, there are activators that will bring about rapid conversion of the starting material, but the desired product is produced in low amounts inasmuch as the activator changes the selective nature of the hydrogenation.

A scheme of this type of behavior can be shown as follows:

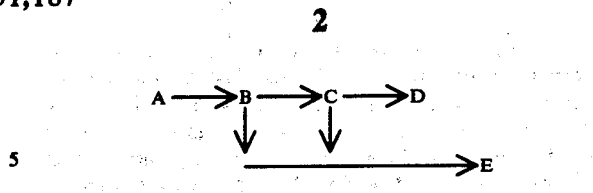

In the above scheme A is nitrobenzene, B is nitrosobenzene, C is phenylhydroxylamine, D is para-aminophenol and E is aniline.

In the first case described, the activator can increase the rate of conversion of A to B to C and thence to D. However, another activator can modify the second pathway with the result that B or C will go to E instead. For instance, we have found that some activators such as iron, nickel, cobalt, manganese and chromium cause B and C to go to E quite readily whereas others will cause the B to D pathway to predominate.

We have found that it is possible to accelerate the step A to D, while minimizing step C to E by using as activators compounds of aluminum, magnesium, silicon, and boron and their halides (fluorides, chlorides, bromides).

Further, and surprisingly, the halide of the catalyst metal itself has been found to be an activator for the A→D reaction. This is not due to the additional metal added, but to a synergistic effect, with the result that improved results are brought about over and above the sum of the two metals that were added.

The hydrogenation catalyst comprises about 5% platinum group metal wherein from 10 to 80% of said platinum group metal is in the form of a salt selected from the group of $RhCl_3$ and $RhBr_3$, preferably $RhCl_3$, and from 20 to 90% of said platinum group metal is in elemental form and where the balance of said catalyst comprises carbon to convert substantially 85 to 100% of the nitrobenzene to a para-aminophenol in an aqueous phase containing the latter. A preferred embodiment of such a catalyst includes a 5% Rh catalyst which is comprised of about 39% Rh in the form of $RhCl_3$ and about 61% Rh in the form of elemental Rh. The platinum group metal in elemental form is either rhodium, platinum, palladium, or ruthenium.

The process of preparing and using the novel catalyst of this invention comprises the following steps:

Charging to a reactor kettle flushed with nitrogen:
1. Aqueous sulfuric acid
2. Activator
3. Activated carbon
4. An aqueous mixture of catalyst metal halide, catalyst on carbon, and quaternary agent.
5. Displacing nitrogen with hydrogen and adding nitrobenzene slowly to rapidly agitated mixture while passing hydrogen thru kettle until desired amount is absorbed.
6. Separate aqueous phase and isolate —aminophenol.

I have also found that it is possible to overcome disadvantages of prior-art techniques in the production of para-aminophenol by the catalytic reduction with hydrogen of nitrobenzene (or nitrobenzenes) in the presence of a hydrogenation catalyst of the platinum-group-metal selected from the group consisting of Pt, Pd, Rh and Ru type (i.e. metal or metal oxide), when the reaction is initially carried out substantially to completion and, prior to removal of the reactants fresh nitrobenzene required for the next reaction is added with agitation to extract intermediates and separate the catalyst from the aqueous phase, this agitation-extraction step using fresh nitrobenzene.

More particularly, the invention resides in a semicontinuous (or continuous if the catalyst presence in the reactor is considered) process in which the aqueous phase is removed from the reaction vessel leaving the nitrobenzene introduced after the hydrogenation action has been terminated by cutoff of the hydrogen feed to the reaction vessel. The nitrobenzene phase thus remaining serves to cover or suspend the catalyst which is also retained in the reactor.

My improved method thus comprises the steps of reacting a system of nitrobenzene, sulfuric acid, water and a surfaceactive agent of a type well known in the art and described, for example, in the aforementioned patent, with hydrogen in the presence of a hydrogenation catalyst to substantial completion of the reaction (85 to 100% conversion of the nitrobenzene to para-aminophenol), terminating the hydrogen feed to the reaction vessel after 4 to 12 hours when the amount of hydrogen reacted is in a ratio substantially of 1.8 to 2.2 moles of $H_2$ to each mole of nitrobenzene, thereafter (subsequent to termination of hydrogen feed and cutoff of the reaction) introducing a change of the fresh nitrobenzene required for the next reaction to agitate the contents of the reaction vessel without removal of the reaction product prior to this point, permitting the contents of the reaction vessel to settle, removing the aqueous phase (containing the para-aminophenol), and adding a new feed stock consisting of surfactant, water and sulfuric acid and again with the nitrobenzene which was added subsequent to the first reaction, serving as part of the total raw material for the production of para-aminophenol for the second reaction. The process is repeated for as many times as is consistent with the useful life of the catalyst and has been found to increase materially the life of the latter by comparison with systems in which the entire batch is removed from the reactor and processed elsewhere. The yield is also improved by comparison with systems in which the reaction is terminated prematurely to retain sufficient nitrobenzene in the reactor to suspend or cover the catalyst.

The reaction may be carried out at temperatures and pressures within the ranges given in the aforementioned patent but preferably at temperatures of 80 to 110° C and pressures of 1 to 3 atmospheres.

The nitrobenzene introduced into the reactor prior to removal of the reaction product but after termination of the reaction acts as a solvent which gives surprising and unanticipated results. I have found it to be particularly advantageous to add a fresh nitrobenzene charge equal to 10 to 30% of the nitrobenzene required for the next reaction.

For example, in practice when the product is removed from the reactor and separated under prior art principles, the para-aminophenol is recovered in the form of purplish or dark crystals. However, when the nitrobenzene is used as a solvent at the termination of the reaction stage, the step of introducing the nitrobenzene while the reaction product remains in the vessel and after termination of the reaction, appears to bring about an effect equivalent to that of solvent extraction of the aqueous phase so that the para-aminophenol crystals are obtained with a white to cream hue and hence with greater purity as is especially desirable when the product is to be used as a precursor for pharmaceuticals.

The yield, based upon the nitrobenzene present at the start of the reaction is 70 to 90%.

The nitrobenzene may be substituted to some extent and I have found that corresponding aminophenols can be made from monomethyl, dimethyl and trimethyl nitrobenzene as well as other substituted nitrobenzenes.

Substituted nitrobenzenes which have been successfully converted to the corresponding aminophenols according to the present invention include:
2-methylnitrobenzene,
3-methylnitrobenzene,
2,3-dimethylnitrobenzene,
2,5-dimethylnitrobenzene,
2,3,5-trimethylnitrobenzene,
2-ethylnitrobenzene,
3-ethylnitrobenzene,
2,3-diethylnitrobenzene,
2,5-diethylnitrobenzene,
2,3,5-triethylnitrobenzene.

According to another aspect of the invention, the recovery of the para-aminophenol of high purity is carried out by treating the aqueous phase, which may contain some aniline sulfate with ammonia ($NH_3$) to bring the aqueous phase to a pH of about 7, thereby separating both the para-aminophenol and the aniline, and thereafter washing the para-aminophenol crystals free from aniline with a mixture of toluene and methanol. The mixture of toluene and methanol represents one of a number of hydrocarbon-alcohol mixtures which can be used for washing the para-aminophenol. Aniline is recovered from the hydrocarbon phase of the washing mixture by distillation.

We have found that rhodium chloride can act as a synertgistic activator for commercial 5% Rh, Pt, Pd or Ru on carbon (Table 1). We have found that the use of rhodium chloride equal in rhodium to the total amount of rhodium in the 5% rhodium on carbon plus rhodium chloride does not hydrogenate as well as the catalyst and activator together. Also the use of 5% Rh/carbon containing as much rhodium does not act as well either. It appears that the concurrent use of the Rh/carbon plus the rhodium chloride results in a more active catalyst. There is thus a pronounced synergistic action.

EXAMPLE I

Nitrobenzene was hydrogenated in a 5 liter creased flask having four vertical creases to act as baffles and equipped with a stirrer which was operated at 600 rpm. The flask was provided with a heating jacket, inlet and outlet tubes for hydrogen, a manometer and an inlet for introducing a solution of nitrobenzene. Into the flask was placed 1800 ml. of water, 235 g. of concentrated sulfuric acid, 50 mg. of aluminum hydroxide, 1g. of boron trifluoride etherate, 10 g. of activated carbon (Nuchar SN) and a mixture of 1.9 g. of 5% Rh/carbon (commercial), 150 mg. $RhCl_3$ (40% Rh) and 2.0 g. of tallow trimethyl ammonium bromide. (Total Rh in flask was 155 mg.).

The reactor was flushed with hydrogen and heated to 92° C. Nitrobenzene (270 g.) was slowly added at the rate of 35–45 ml. per hour while at the same time adding hydrogen at such a rate that the pressure in the flask remained essentially constant. Temperature was maintained at 90°–95° C.

About 100 liters of hydrogen was absorbed in eight hours, after which time a slowing in absorption was noted. The solution then contained 32 g. of unreacted nitrobenzene, 174 g. para-aminophenol, and 13 g. of aniline, equivalent to 84.5% PAP and 7.0% aniline.

EXAMPLE II

The above experiment was repeated with the following changes: instead of the 1.9 g. of 5% Rh/carbon an alternate amount of 5% Rh/carbon was used amounting to 3.11 g. containing the same total amount of Rh (155 mg.) as above. The absorption rate of the hydrogen was one half that of the previous run. After 16 hours the solution contained 75% PAP and 19% aniline, based on the nitrobenzene reacted.

EXAMPLE III (Substitution of tin for rhodium activator).

A known activator for platinum or palladium catalysts is stannous chloride. This activator was used as in Example II, by charging 150 mg. stannous chloride with the 3.1 g. 5% 5% Rh/carbon. No rhodium chloride was used.

The hydrogenation proceeded very rapidly being essentially complete in six hours, however, the resultant solution contained 112 g. of para-aminophenol and 91 g. of aniline based on nitrobenzene reacted for equivalent yields of 53% PAP and 50% aniline.

EXAMPLE IV

An equal amount of Rh (155 mg.), added as $RhCl_3$, was substituted for all the Rh as in Example I. The rate of hydrogen uptake was comparatively slower, taking 25 hours for an equivalent amount of hydrogen to be absorbed. Rhodium chloride can be seen therefore to be an activator for commercial rhodium on carbon, having synergistic activity. This is shown in Table 1.

Table 1

| Catalyst | Total Rh (mg.) | Hydrogenation Time (relative) (a) (hours) |
| --- | --- | --- |
| 5% Rh/c | 155 | 1.9 |
| 5% Rh/c + $RhCl_3$ | 155 | 1 |
| $RhCl_3$ | 155 | 4.5 |

(a) for same conversion of nitrobenzene.

EXAMPLE V

The same procedure and reaction conditions as in Example I were employed here except that 40 mg. of $RhCl_3$ were used instead of 150 mg. and that 2.78 g. of 5% Rh/C (commercial catalyst) were used instead of 1.9 g. Again, the yield of para-aminophenol was as in Example I.

EXAMPLE VI

The same procedure and reaction conditions as in Example I were employed here except that 300 mg. of $RhCl_3$ were used instead of 150 mg. and that 0.70 g. 5% Rh/c (commercial catalyst) were used instead of 1.9 g. Again, the yield of para-aminophenol was as in Example I.

EXAMPLE VII

The same procedures and reaction conditions as in Example I were employed except that 1.9 g. of 5% Pt/C (commercial catalyst) were used instead of 1.9 g. of 5% Rh/C. The results are tabulated in Table II.

Table II

| Catalyst | Reaction Time (relative) |
| --- | --- |
| Pt/C | 1.4 |
| Pt/C - $RhCl_3$ | 1.0 |
| $RhCl_3$ | 6 |

EXAMPLE VIII

The same procedures and reaction conditions as in Example I were employed except that 1.9 g. of 5% Pd/C (commercial catalyst) were used instead of 1.9 g. of 5% Rh/C. The results are tabulated in Table III.

Table III

| Catalyst | Reaction Time (relative) |
| --- | --- |
| Pd/C | 1.8 |
| Pd/C - $RhCl_3$ | 1.0 |
| $RhCl_3$ | 5 |

I claim:

1. A method of preparing aminophenol comprising the steps of:
    a. hydrogenating a nitrobenzene substantially to completion by feeding hydrogen to a reaction mixture containing the nitrobenzene in the presence of aqueous sulfuric acid and a hydrogenation catalyst which comprises platinum group metal wherein from 10 to 80% of said platinum group metal is in the form of a rhodium salt selected from the group which consists of $RhCl_3$ and $RhBr_3$ and from 20 to 90% of said platinum group metal is in the form of elemental Rh, Pt, Pd or Ru and wherein the balance of said catalyst comprises carbon to produce a para-aminophenol in an aqueous phase containing the latter at a temperature of from 80 to 110° C and at 1 to 3 atmospheres;
    b. terminating hydrogen feed to said reaction mixture:
    c. thereafter charging the reaction mixture with a quantity of fresh nitrobenzene as required to repeat step (a);
    d. thereafter premitting said aqueous phase to separate from the nitrobenzene phase;
    e. next removing said aqueous phase from said reactor while retaining said nitrobenzene phase and said catalyst therein;
    f. thereafter adding fresh sulfuric acid to the reactor;
    g. repeating steps (a) through (f) in succession to transform nitrobenzene semicontinuously into said para-aminophenol; and
    h. recovering the para-aminophenol thus formed from the aqueous phases removed from said reactor.

2. The method defined in claim 1 wherein the 5% platinum group metal in the catalyst is comprised of about 39% Rh in the form of $RhCl_3$ and about 61% Rh in the form of elemental Rh.

3. The method defined in claim 1 wherein the rate of absorption of hydrogen is from 1.8 to 2.2 moles of $H_2$/mole of nitrobenzene over a period of from 4 to 12 hours.

4. The method defined in claim 1 wherein during step (b) the fresh nitrobenzene introduced into the reaction mixture is equal to from 10 to 30% of the nitrobenzene required for the next reaction.

* * * * *